(12) United States Patent
Unwin et al.

(10) Patent No.: US 7,241,313 B2
(45) Date of Patent: Jul. 10, 2007

(54) SURGICAL IMPLANT

(75) Inventors: Paul Unwin, Middlesex (GB); Gordon Blunn, Middlesex (GB); Michael Herbert Jacobs, Birmingham (GB); Mark Andrew Ashworth, Birmingham (GB); Xinhua Wu, Birmingham (GB)

(73) Assignee: Stanmore Implants Worldwide Limited, Stanmore, Middlesex (GB)

( * ) Notice: Subject to any disclaimer, the term of this patent is extended or adjusted under 35 U.S.C. 154(b) by 126 days.

(21) Appl. No.: 10/486,627

(22) PCT Filed: Aug. 12, 2002

(86) PCT No.: PCT/GB02/03723

§ 371 (c)(1),
(2), (4) Date: Jun. 22, 2004

(87) PCT Pub. No.: WO03/013396

PCT Pub. Date: Feb. 20, 2003

(65) Prior Publication Data

US 2004/0243237 A1  Dec. 2, 2004

(30) Foreign Application Priority Data

Aug. 11, 2001 (GB) ................................. 0119652.6

(51) Int. Cl.
*A61F 2/44* (2006.01)
(52) U.S. Cl. ................................. 623/17.11
(58) Field of Classification Search ........ 606/17.11–16
See application file for complete search history.

(56) References Cited

U.S. PATENT DOCUMENTS 3,855,638 A * 12/1974 Pilliar ..................... 623/23.55
4,542,539 A * 9/1985 Rowe et al. ............. 623/23.57
5,171,281 A * 12/1992 Parsons et al. .......... 623/17.15
5,306,309 A * 4/1994 Wagner et al. ........... 623/17.16
5,344,494 A * 9/1994 Davidson et al. ............... 134/7
5,368,881 A * 11/1994 Kelman et al. ............ 427/2.26
5,458,643 A * 10/1995 Oka et al. ................ 623/17.16
5,658,333 A * 8/1997 Kelman et al. ............ 623/23.6

(Continued)

FOREIGN PATENT DOCUMENTS

RU    2218242    * 11/1999

(Continued)

*Primary Examiner*—Eduardo C. Robert
*Assistant Examiner*—Annette Reimers
(74) *Attorney, Agent, or Firm*—Fulbright & Jaworski L.L.P.

(57) ABSTRACT

A surgical implant comprises a core region and a porous surface region extending over at least part of the core region. The surface region has a predetermined pore volume fraction. A method of manufacturing a surgical implant comprises: (i) loading metallic powder having a predetermined particle size distribution around a pre-formed core in a sealable capsule; (ii) reducing pressure within the capsule to a predetermined pressure below atmospheric pressure; (iii) pressurising the capsule with a process gas to a predetermined pressure higher than the predetermined pressure of step (ii); (iv) sealing the capsule; (v) heating the pressurised sealed capsule at an elevated temperature and an elevated pressure for a predetermined time to produce an implant precursor; (vi) cooling the sealed capsule, and; (vii) heating the implant precursor for a predetermined time at an elevated temperature and a predetermined pressure below atmospheric pressure, whereby to generate porosity in the implant precursor.

22 Claims, 2 Drawing Sheets

U.S. PATENT DOCUMENTS

| | | | |
|---|---|---|---|
| 5,986,169 A * | 11/1999 | Gjunter | 424/422 |
| 6,149,688 A * | 11/2000 | Brosnahan et al. | 623/23.5 |
| 6,206,924 B1 * | 3/2001 | Timm | 623/17.16 |
| 6,398,811 B1 * | 6/2002 | McKay | 623/17.16 |
| 6,471,725 B1 * | 10/2002 | Ralph et al. | 623/17.16 |
| 6,602,291 B1 * | 8/2003 | Ray et al. | 623/17.11 |
| 6,706,067 B2 * | 3/2004 | Shimp et al. | 623/17.11 |
| 6,736,849 B2 * | 5/2004 | Li et al. | 623/17.11 |

FOREIGN PATENT DOCUMENTS

WO     WO 92/21302    * 10/1992

* cited by examiner

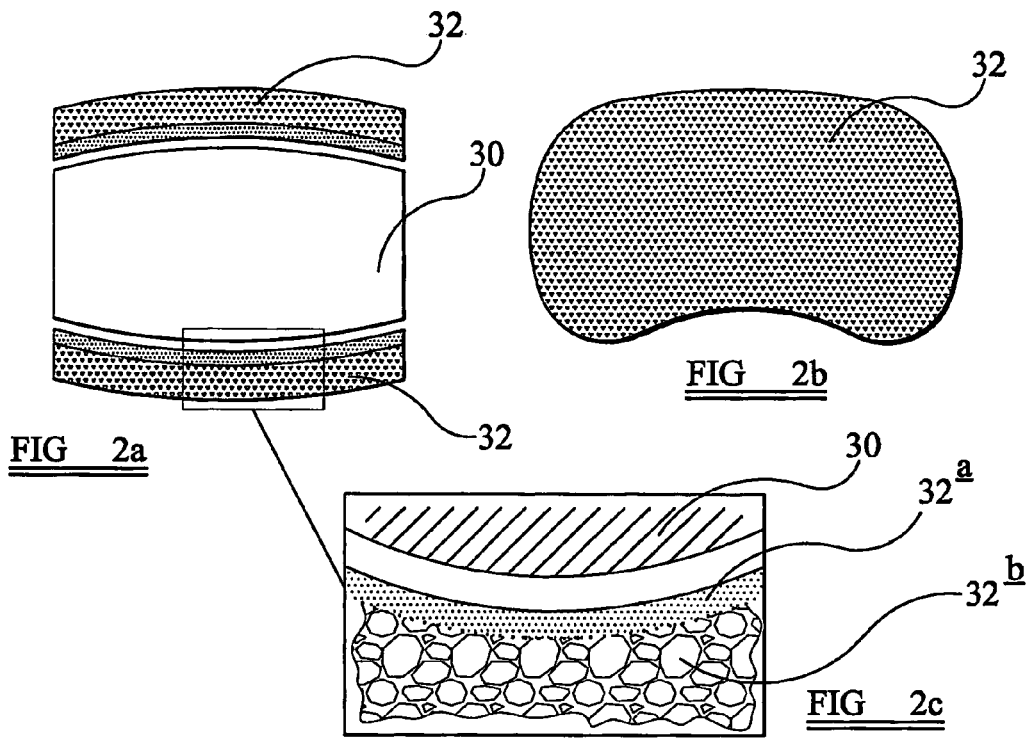
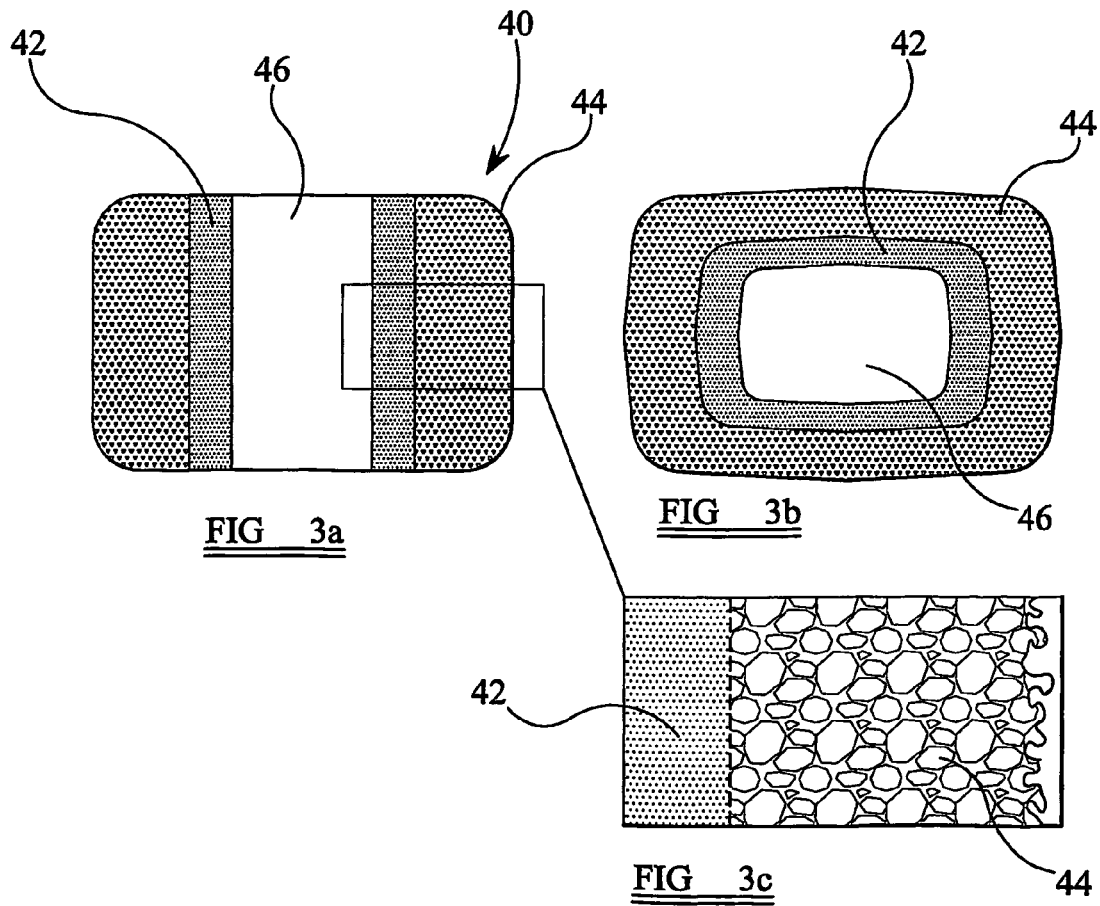

SURGICAL IMPLANT

BACKGROUND OF THE INVENTION

The present invention relates to a surgical implant and to methods of making the same.

There are many different types of surgical implants and devices, including orthopaedic implants (hip, shoulder, knee, ankle, elbow), cranio-facial implants and spinal implants (such as a spinal cage or spinal disc). Such implants are commonly made from biocompatible metals such as titanium, titanium-based alloys, stainless steel or cobalt-chromium alloys, depending on strength and weight considerations. Another consideration, particularly for implants which replace bone, is the elastic modulus of the implant. The closer the modulus of elasticity is to natural bone, the better the stress redistribution to adjacent bone. Better stress distribution results in prolonged useful life of the implant.

To increase bonding of surrounding tissues with an implant, it is known to apply a coating to the surface of the implant, by for example plasma spraying, which roughens the surface of the implant. The coating may be of a different composition to the implant to improve wear resistance and/or to provide enhanced biocompatibility (eg. TiN is extremely inert and can be applied as a coating to aluminium- or vanadium-containing implants to prevent leaching of those metals from the implant.

SUMMARY OF THE INVENTION

It is an object of the present invention to provide an improved surgical implant, which preferably has improved bone compatibility and/or wear resistance and/or useful life and/or is stronger than known implants.

According to the present invention, there is provided a surgical implant comprising:
(i) a core region, and
(ii) a porous surface region extending over at least a part of said core region,
wherein the porous surface region has a predetermined pore volume fraction.

It will be understood that as used herein, "pore volume fraction" of a porous region is a ratio of pore volume in that region to the total volume of that region, expressed as a percentage.

The implant may be any shape as necessitated by its intended application. For example the implant may be elongate (eg. cylindrical) or disc-shaped. The implant may have an irregular shape, and the porous surface region may vary in thickness over the core region.

Preferably, the pore volume fraction within the porous surface region is 20 to 50%. The predetermined pore volume fraction is chosen according to the nature of the implant. A higher pore volume fraction results in a lighter implant with a lower modulus of elasticity.

Preferably, the pores are interconnected and substantially uniformly distributed within the porous surface region. Preferably, at least some (and preferably the majority) of the pores have a size in the range of from 100 μm to about 750 μm, and more preferably from about 200 μm to 500 μm.

Preferably, the porous surface region is at least about 1 mm thick, and is more preferably from about 2 mm to about 5 mm thick, most preferably 2 mm to 3 mm thick.

Distinct regions within the porous surface region may have a different pore size distribution and/or a different pore volume fraction such that there is a pore size and/or pore volume fraction gradient within the porous surface region. For example, there may be a pore volume fraction gradient along an axis of the implant and/or perpendicular to the axis of the implant.

The core region may be fully dense or porous. The degree of porosity of the core region may be more than, less than or the same as the surface region.

Preferably, the core region is relatively less porous than the surface region.

Preferably, the core region has a density of from 0.7 to 1.0 of theoretical density (i.e. from 0 to 30% porosity).

The core region and the porous surface region may be constructed from the same or different materials. Particularly suitable materials include titanium (eg. commercial purity [ASTM B 338 GR 2] titanium), stainless steel, titanium-based alloys (eg. Ti—Al—V alloys and Ti—Al—Nb alloys) and cobalt-chromium based alloys.

Particularly preferred materials are commercial purity titanium, Ti-6Al-4V, Ti-6Al-7Nb, Stellite 21 and stainless steel 316L.

Preferably, the porous surface region is diffusion bonded to the core region. Thus, it will be understood that the interface between the core region and the porous surface region does not introduce a weakness into the implant.

According to a second aspect of the invention, there is provided a method of manufacturing a surgical implant in accordance with said first aspect comprising the steps of:
(i) loading metallic powder having a predetermined particle size distribution around a pre-formed core in a sealable capsule,
(ii) reducing pressure within said capsule to a predetermined pressure below atmospheric pressure,
(iii) pressurising said capsule with a process gas to a predetermined pressure higher than the predetermined pressure of step (ii),
(iv) sealing said capsule,
(v) heating said pressurised sealed capsule at an elevated temperature and an elevated pressure for a predetermined time to produce an implant precursor,
(vi) cooling said sealed capsule, and
(vii) heating said implant precursor for a predetermined time at an elevated temperature and a predetermined pressure below atmospheric pressure, whereby to generate porosity in said implant precursor.

Preferably, the powder used in step (i) has a particle size range of from about 50 μm to about 750 μm (i.e. substantially all the particles are within the specified size range). The powder may be produced, for example, by gas atomisation or mechanical attrition.

Conveniently, the core may be integral with the capsule, although the core may be free standing. In either case, the core may be of the same or different material to the powder and of the same or different material to the rest of the capsule.

Preferably, the predetermined pressure of step (ii) is $10^{-3}$ mbar (0.1 Pa) or less. Preferably, the predetermined pressure of step (vii) is $10^{-3}$ mbar (0.1 Pa) or less.

The process gas of step (iii) may be an unreactive gas (eg. argon), or a reactive gas (eg. nitrogen), or a mixture of reactive and unreactive gases, the unreactive gas serving as a carrier or diluent for the reactive gas. When nitrogen is present in the process gas, the surfaces of the eventually formed pores become nitrided thereby increasing wear resistance and chemical inertness. Use of nitrogen is particularly advantageous when the metallic powder contains titanium. As an alternative, a separate nitriding step may be carried out after step (vii), preferably at a pressure of from about 800° C. to about 1000° C. and at a pressure of from about 10 to 100 MPa for 1 to 8 hours.

Preferably the pressure of step (iii) is from about 1 bar ($1 \times 10^5$ Pa) to about 5 bar ($5 \times 10^5$ Pa) positive pressure.

Preferably, the elevated temperature of step (v) is from about 850 to about 1100° C. Preferably, step (v) is carried out over a period of from about 1 hour to about 4 hours.

In step (vi), the sealed capsule (and the implant precursor therein) is preferably cooled to room temperature. Step (vii) may be performed on the implant precursor in the capsule. Alternatively, the implant precursor can be separated from the capsule after step (vi) prior to step (vii). The capsule is conveniently removed by, for example, machining it off on a lathe. Preferably, the elevated temperature of step (vii) is from about 900 to about 1300° C. Preferably, step (vii) is carried out for no more than about 80 hours, preferably no more than about 60 hours, and even more preferably no more than about 48 hours. Preferably, step (vii) is carried out for at least 6 hours and more preferably for at least 12 hours.

If step (vii) is performed with the precursor implant in the capsule, the capsule is separated from the implant after step (vii), by for example machining.

It will be understood that the implant formed by the above method will have the shape of the interior surfaces of the capsule so that additional machining steps may be required to obtain the final required shape for the implant. However, an implant having a shape substantially as required can be produced by using a capsule having an appropriately shaped interior surface. Examples of methods by which an appropriately shaped capsule can be made include electro-forming and direct laser fabrication.

In a slight modification of the above method, the metallic powder is partly consolidated prior to encapsulation. This may be achieved by, for example, selective laser sintering a mixture of the metallic powder and a polymeric binder. Different powder fractions may be used to form different regions of the implant, and so this modification is particularly useful for making implants having a gradient porosity within the porous region.

According to a third aspect of the present invention, there is provided a further method of manufacturing a surgical implant of said first aspect, comprising the steps of:

(i) selectively sintering successive layers of metallic particles whereby to form an implant precursor of required shape, and (ii) heating said implant precursor whereby to form said implant.

Preferably, step (ii) is effected under reduced pressure, for example in a vacuum oven.

Step (i) may be effected by sintering the particles around a core. Preferably, said core is from 0.7 to 1.0 of theoretical density (i.e. has a porosity of from 0 to 30%). However, the core may have the same, higher or lower density, than the resultant porous surface region.

Preferably, substantially all said metallic particles have a size of 750 µm or less, more preferably 500 µm or less and most preferably 150 µm or less. Preferably, said particles have a size of at least 50 µm. Preferably, said metallic particles are in admixture with a binder such as a light and/or heat sensitive polymeric binder. More preferably, step (i) is effected by scanning a laser (typically of power 20 to 40 W) over said mixture of metallic powder and binder.

Preferably, step (ii) is effected from about 1000° C. to about 1300° C. It will be understood that in step (ii), any binder present is burnt off.

It will be understood that step (i) can be effected to give regions of macroporosity. For example, the laser sintered region can be provided with recesses extending inwardly from the surface of the implant, and/or chambers within the implant. In addition, said chambers and/or recesses may be interconnected to provide channels or passages in the implant. It will also be understood that such macroporosity can be introduced into the implant produced by the modified method of the second aspect which uses selective laser sintering.

BRIEF DESCRIPTION OF THE DRAWINGS

Embodiments of the invention will now be described by way of example only, with reference to the accompanying drawings in which:

FIGS. 2a is a schematic sectional representation of a replacement lumbar spinal disc in accordance with the present invention, FIG. 2b is a plan view of the disc of FIG. 2a, FIG. 2c is a detail view of FIG. 2a, FIG. 3a is a schematic sectional representation of a spinal cage in accordance with the present invention, FIG. 3b is a plan view of the cage of FIG. 3a, and FIG. 3c is a detail view of FIG. 3a.

DETAILED DESCRIPTION OF THE INVENTION

EXAMPLE 1

Figure 1:
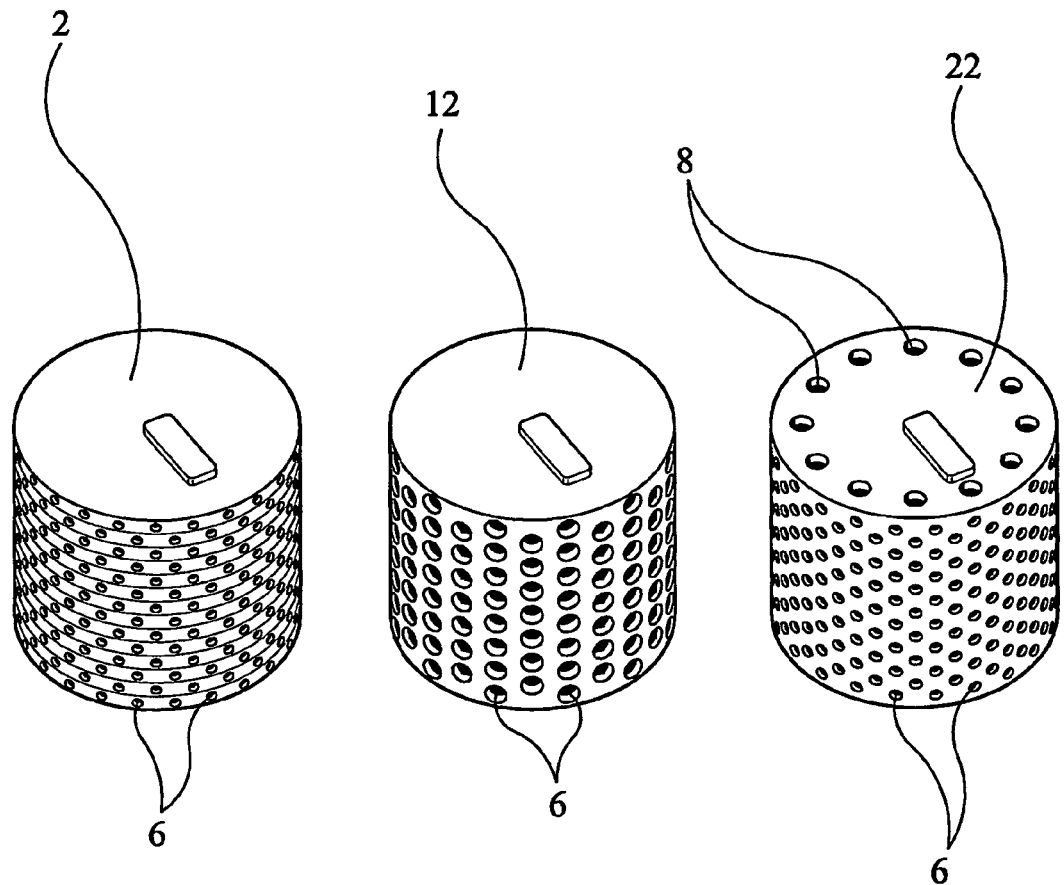
FIG. 1 is a photograph showing how macroporosity can be introduced by the method according to the third aspect of the invention.

A 100 mm long cylindrical container of commercial purity titanium (ASTM B 338 GR 2) having an internal diameter of about 22 mm and an external diameter of 25.4 mm was filled with a gas atomised powder consisting of particles of Ti-6Al-4V alloy (Crucible Research, USA) having a predetermined particle size distribution. Where necessary, the powder was passed through sieves of appropriate mesh to obtain a particular particle size fraction. The container was filled without vibration, i.e. to "tap density" only. Air was evacuated from the container (pressure<0.1 Pa) and back-filled with argon ($10^5$ Pa positive pressure) for 2 minutes. After sealing, the container was HIPped for 4 hours at 950° C. at an external pressure of 100 MPa. Subsequently, the container was allowed to cool to room temperature and atmospheric pressure, Ar remaining under pressure in the alloy matrix. The implant precursor was machined out of the container and heat treated at 1050° C. for 48 hours under vacuum (<0.1 Pa).

The degree of porosity in the resultant implant is given for different powder fractions in Table 1 below.

TABLE 1

| Ex. | Powder (µm) | Porosity (%) | Mean pore size (µm) | Size Distribution of Pores (µm) | | | | |
|---|---|---|---|---|---|---|---|---|
| | | | | >350 | >250 | >150 | >100 | >50 |
| 1a | <125 | 32 ± 2.3 | 32 | — | — | — | 4 | 47 |
| 1b | <150 | 32.1 ± 1.0 | 43 | — | — | — | 6 | 51 |
| 1c | <500 | 31.3 ± 2.0 | 49 | — | — | 2 | 14 | 59 |
| 1d | 125–150 | 34 ± 1.5 | 61 | — | — | 6 | 22 | 68 |
| 1e | 150–180 | 34.6 ± 2.0 | 74 | — | 1 | 14 | 33 | 72 |
| 1f | 180–250 | 27.8 ± 2.7 | 72 | — | 1 | 13 | 34 | 73 |
| 1g | 150–250 | 34.2 ± 3.0 | 72 | 0.2 | 2 | 14 | 31 | 72 |
| 1h | 150–500 | 34.2 ± 1.7 | 102 | 1.3 | 3 | 20 | 41 | 76 |

TABLE 1-continued

| Ex. | Powder (μm) | Porosity (%) | Mean pore size (μm) | Size Distribution of Pores (μm) | | | | |
|---|---|---|---|---|---|---|---|---|
| | | | | >350 | >250 | >150 | >100 | >50 |
| 1i | 250–425 | 28.2 ± 1.9 | 119 | 1.5 | 8 | 28 | 48 | 80 |
| 10 | 250–500 | 33.2 ± 2.5 | 118 | 2.2 | 9 | 28 | 46 | 77 |
| 1j | 425–500 | 20.1 ± 2.2 | 116 | 1.7 | 9 | 27 | 45 | 77 |
| 1k | 500–750 | 20.7 ± 3.6 | 111 | 2.6 | 9 | 24 | 41 | 69 |

EXAMPLE 2

Example 1 was repeated using powders having a size distribution of 180–250 μm and 150–500 μm. HIPping was carried out at 1000° C. and subsequent heat treatment (after removal from the container) was at 1050° C. for 48 hours. The results are shown in Table 2.

TABLE 2

| Ex. | Powder (μm) | Porosity (%) | Mean pore size (μm) | Size Distribution of Pores (μm) | | | | |
|---|---|---|---|---|---|---|---|---|
| | | | | >350 | >250 | >150 | >100 | >50 |
| 2a | 180–250 | 40.7 ± 3.3 | 96 | 0.3 | 6 | 27 | 47 | 80 |
| 2b | 150–500 | 38.8 ± 2.1 | 117 | 1.3 | 7 | 27 | 48 | 78 |

EXAMPLE 3

Example 1 was repeated using a powder having a size distribution of 250–500 μm. HIPping was carried out at 1000° C. and subsequent heat treatment (after removal from the container) was at 1050° C. from 12 up to 48 hours. The results are shown in Table 3.

TABLE 3

| Ex. | Treatment Time (hr) | Porosity (%) | Mean pore size (μm) | Size Distribution of Pores (μm) | | | | |
|---|---|---|---|---|---|---|---|---|
| | | | | >350 | >250 | >150 | >100 | >50 |
| 3a | 12 | 33.2 ± 1.5 | 117 | 2.9 | 9 | 26 | 44 | 77 |
| 3b | 24 | 33.8 ± 2.1 | 120 | 3.0 | 10 | 28 | 46 | 76 |
| 3c | 36 | 36.1 ± 3.0 | 123 | 4.2 | 12 | 28 | 44 | 76 |
| 3d | 48 | 33.2 ± 2.5 | 118 | 2.2 | 9 | 28 | 46 | 77 |

EXAMPLE 4

Example 1 was repeated using a powder having a size distribution of <150 μm. Subsequent heat treatment after removal of the container was at 1050° C. The results are shown in Table 4.

TABLE 4

| Ex. | Treatment Time (hr) | Porosity (%) | Mean pore size (μm) | Size Distribution of Pores (μm) | | | | |
|---|---|---|---|---|---|---|---|---|
| | | | | >350 | >250 | >150 | >100 | >50 |
| 4a | 12 | 4.1 ± 0.7 | 15 | — | — | — | — | — |
| 4b | 24 | 16 ± 3.0 | 24 | — | — | — | — | 7 |
| 4c | 36 | 25.6 ± 5.8 | 27 | — | — | — | 2 | 12 |
| 4d | 48 | 28.3 ± 3.6 | 31 | — | — | — | 3 | 17 |

EXAMPLE 5

Example 1 was repeated using a powder having a size distribution of 250–425 μm. Subsequent heat treatment after removal of the container was for 48 hours at different temperatures. The results are shown in Table 5.

TABLE 5

| Ex. | Treatment Temperature (° C.) | Porosity (%) | Mean pore Size (μm) | Size Distribution of Pores (μm) | | | | |
|---|---|---|---|---|---|---|---|---|
| | | | | >350 | >250 | >150 | >100 | >50 |
| 5a | 1050° C. | 29 ± 1 | 117 | 1.0 | 6 | 27 | 47 | 82 |
| 5b | 1100° C. | 26 ± 1 | 108 | 0.5 | 5 | 23 | 43 | 80 |
| 5c | 1150° C. | 26 ± 3 | 102 | 0.2 | 4 | 20 | 41 | 73 |

EXAMPLE 6

Example 1 was repeated with various powders. After the heat treatment (1100° C. for 48 hours) the implants were pressure nitrided, in pure nitrogen, at 950° C. and 50 MPa for 6 hours to coat the internal surface of the pores with a thin layer of titanium nitride. The results are shown in Table 6.

TABLE 6

| Ex. | Powder (μm) | Porosity (%) | Mean pore size (μm) | Size Distribution of Pores (μm) | | | | |
|---|---|---|---|---|---|---|---|---|
| | | | | >350 | >250 | >150 | >100 | >50 |
| 6a | <125 | 44.7 ± 3.7 | 69 | 0 | 0 | 3 | 16 | 62 |
| 6b | 125–150 | 44.8 ± 4.7 | 93 | 0 | 1 | 14 | 38 | 77 |
| 6c | 150–180 | 40.8 ± 2.7 | 107 | 1.0 | 4 | 21 | 43 | 80 |
| 6d | 180–250 | 34.7 ± 3.1 | 114 | 0.4 | 3 | 23 | 41 | 70 |
| 6e | 250–425 | 31.2 ± 2.6 | 146 | 5 | 15 | 37 | 59 | 89 |
| 6f | 425–500 | 21 ± 3.1 | 143 | 3 | 13 | 39 | 61 | 86 |

EXAMPLE 7

A 12.7 mm solid cylindrical core of Ti-6Al-4V was centrally placed in the titanium container described above for Example 1. The space between the core and the inner cylinder wall was filled with Ti-6Al-4V powder (particle size 500–710 μm). The container was evacuated and back-filled with Ar to $10^5$ Pa positive pressure, sealed and HIPped at 950° C. for 4 hours at 100 MPa. Subsequent heat treatment after removal from the container was at 1050° C. for 48 hours. This resulted in a sample having a porous coating of 29±5% porosity with 43% of pores>50 μm, 16%>100 μm and 6%>150 μm.

EXAMPLE 8

Example 1 was repeated using powder having a particle size <125 μm. After HIPping the part is machined to remove the container and to reduce the diameter of the part to ~17 mm. Unlike Example 1, no heat treatment was carried out at this stage. The resultant cylinder was then used as the core in the same way as Example 7, the container having an external diameter of 38.1 mm and an internal diameter of approx 35 mm. Example 7 was then repeated, the core being surrounded in this case with 250–425 μm size powder. The resultant implant had a porous core with a mean pore size of 26 μm (28.9±2.10% porosity) and a porous outer layer with a mean pore size of 113 μm (24.9±1.9% porosity).

Example 8 demonstrates the ability of the method to produce implants having predetermined regions of differing porosity in a controllable manner. In addition, it will be understood that the procedure can be extended to produce an implant having more than 2 different layers of differing porosity, i.e. graded porous structures can be manufactured.

EXAMPLE 9

Example 1 was repeated using powder having a predetermined size distribution. After the heat treatment (1100° C. for 48 hours), samples were machined into tensile test pieces such that the properties of the porous material could be assessed. The results are shown in Table 7.

TABLE 7

| Ex. | Powder (μm) | Porosity (%) | UTS (MPa) | E (GPa) | Elongation (%) | 0.2% PS (MPa) | 0.3% PS (MPa) |
|---|---|---|---|---|---|---|---|
| 7a | <500 | 24.6 | 386 | 58 | 1 | 346 | 367 |
| 7b | 125–150 | 25.7 | 437 | 60 | 1.1 | 383 | 398 |
| 7c | 150–250 | 26.2 | 435 | 64 | 0.8 | 384 | 399 |
| 7d | 250–500 | 27.5 | 493 | 74 | 1.8 | 420 | 439 |

EXAMPLE 10

In order to demonstrate that in the Examples where a pre-formed core is bonded to a porous surface region, there is a strong bond at the interface between the core and surface regions, tensile strength tests where carried out. In these tests, the powder (Ti-6Al-4V) was simultaneously consolidated and diffusion bonded to a solid Ti-6Al-4V bar such that the interface was at the midpoint of the gauge length of the sample. Two powder fractions were assessed, 125–150 μm (test sample a) and 150–250 μm (test sample b). In each case, the sample container was backfilled with Ar to $10^5$ Pa positive pressure. The initial HIP stage was carried out at 950° C. for 4 hours at 100 MPa. The subsequent heat treatment stage was carried out at 1100° C. for 48 hours. The resultant porosity was about 40% (test sample a) and 35% (test sample b).

In both cases the tensile UTS was about 400 MPa and failure occurred remote from the interface within the bulk of the porous material. Routine metallographic investigations confirmed that the interface remained unaffected and that the interface was free of contamination (i.e. oxides) and indistinguishable from the adjacent matrix.

EXAMPLE 11

Referring to FIG. 1, the parts shown were fabricated by selective laser sintering. The laser is controlled by a computer which is loaded with a CAD file containing the configuration of the part. The part was fabricated on a powder bed heated to 160° C. (typical temperature 100–200° C.). Powder of particle size <150 μm and 15% by volume binder (typically 5 to 25% by volume) was heated to 60° C. (typically 50–100° C. and fed onto the powder bed with a build height of 200 μm per layer (typically 100 to 500 μm). Selective sintering was effected using a 25 W laser. After the part had been built up, debinding was effected at 400° C. for 30 minutes (typically 200–500° C. for 30 to 120 minutes) after which sintering was effected at 1100° C. (typically 1000–1350° C.).

As can be seen from FIG. 1, the part 2 has a generally porous cylindrical region (porosity of about 20–25%), with a regular array of round recesses 6 around its outer periphery ("macroporosity"). The recesses 6 are 0.75 mm in circumference and extend inwardly by 3 mm. Part 12 is similar to part 2 except that the recesses 6 are 2 mm in diameter.

Part 22 is also similar to part 2, except that the recesses 6 are 1 mm in diameter and 5 mm deep. In addition, a circular array of channels 8 is provided. Each channel is 1.5 mm in diameter and extends from the top surface of the part to its base.

Referring to FIGS. 2a to 2c, a replacement spinal disc is shown schematically. The disc comprises a per se known biomedical semicrystalline polymeric disc 30 (for example polyurethane or polyethylene) sandwiched between a pair of disc-shaped metallic end plates 32 in accordance with the present invention. The polymeric disc 30 is secured to the end plates 32 by adhesive, although it will be understood that the elements can be fused together or the end plates 32 infiltrated with the polymeric disc 30.

The discs 32 themselves are generally kidney shaped (FIG. 2b) and comprise a substantially non-porous core region 32a adjacent the polymeric disc 30 and a porous outer region (32b), remote from the polymeric disc (30) (FIG. 2c). The porous outer region facilitates tissue in-growth.

Referring to FIGS. 3a to 3c, a spinal cage 40 is generally in the shape of a hollow tuber with a rectangular cross section. A core 42 of substantially fully dense metal is surrounded by a porous outer metal region 44 (facilitating in growth of tissue). A passage 46 extends through the centre of the cage 40.

It will be readily apparent from the foregoing that by careful selection of powder fraction and process parameters, a desired porosity and pore size distribution of the porous surface region can be obtained, according to the particular end application intended for the implant. Although the above Examples are cylindrical rods, it will be understood that they can be readily machined to an appropriate shape depending on the proposed use. Equally, it will be understood that the container used to prepare the implant precursor need not be cylindrical and can be of any desired shape.

The invention claimed is:

1. A method of manufacturing a surgical implant comprising a core region and a porous surface region extending over at least a part of said core region, the porous surface region having a predetermined pore volume fraction, the method comprising the steps of: (i) loading metallic powder having a predetermined particle size distribution around a pre-formed core in a sealable capsule, (ii) reducing pressure within said capsule to a predetermined pressure below atmospheric pressure, (iii) pressurising said capsule with a process gas to a predetermined pressure higher than the predetermined pressure of step (ii), (iv) sealing said capsule, (v) heating said pressurised sealed capsule at an elevated temperature and an elevated pressure for a predetermined time to produce an implant precursor, (vi) cooling said sealed capsule, and (vii) heating said implant precursor for a predetermined time at an elevated temperature and a predetermined pressure below atmospheric pressure, whereby to generate porosity in said implant precursor.

2. A method as claimed in claim 1, wherein the powder used in step (i) has a particle size range of from about 50 μm to about 750 μm.

3. A method as claimed in claim 1, wherein the predetermined pressure of step (ii) is $10^{-3}$ mbar (0.1 Pa) or less.

4. A method as claimed in claim 1, wherein the predetermined pressure of step (vii) is $10^{-3}$ mbar (0.1 Pa) or less.

5. A method as claimed in claim 1, wherein the process gas of step (iii) is an unreactive gas, or a reactive gas, or a mixture of reactive and unreactive gases, the unreactive gas serving as a carrier or diluent for the reactive gas.

6. A method as claimed in claim 5, wherein nitrogen is used as the reactive gas.

7. A method as claimed in claim 1, wherein a nitriding step is carried out after step (vii).

8. A method as claimed in claim 1, wherein the pressure of step (iii) is from about $1\times10^5$ Pa to about $5\times10^5$ Pa positive pressure.

9. A method as claimed in claim 1, wherein the elevated temperature of step (v) is from about 850 to about 1100 C.

10. A method as claimed in claim 1, wherein the elevated temperature of step (vii) is from about 900 to about 1300 C.

11. A method as claimed in claim 1, wherein the implant precursor is separated from the capsule after step (vi) prior to step (vii).

12. A method as claimed in claim 1, wherein the capsule is separated from the precursor implant after step (vii) by machining.

13. A method as claimed in claim 1, wherein the metallic powder is partly consolidated prior to encapsulation, preferably by selective laser sintering a mixture of the metallic powder and a polymeric binder.

14. An implant manufactured by the method of claim 1.

15. An implant as claimed in claim 14, wherein the pore volume fraction within the porous surface region is 20 to 50%.

16. An implant as claimed in claim 14, wherein the pores are interconnected and substantially uniformly distributed within the porous surface region.

17. An implant as claimed in claim 14, wherein at least some of the pores have a size in the range of from 100 μm to about 750 μm.

18. An implant as claimed in claim 14, wherein the porous surface region is at least about 1 mm thick.

19. An implant as claimed in claim 14, wherein distinct regions within the porous surface region have a different pore size distribution and/or a different pore volume fraction such that there is a pore size and/or pore volume fraction gradient within the porous surface region.

20. An implant as claimed in claim 14, wherein the core region has a density of from 0.7 to 1.0 of theoretical density.

21. An implant as claimed in claim 14, wherein the core region and/or the porous surface region are made from titanium, commercial purity [ASTM B 338 GR 2] titanium, stainless steel, titanium-based alloys, Ti—Al—V alloys, Ti—Al—Nb alloys or cobalt-chromium based alloys.

22. An implant as claimed in claim 21, wherein the core region and/or the porous surface region are made from Ti-6Al-4V, Ti-6Al-7Nb, Stellite 21 or stainless steel 316L.

* * * * *